United States Patent [19]

Holyoke, Jr.

[11] 4,309,358

[45] Jan. 5, 1982

[54] AGRICULTURAL STANNANAMINES

[75] Inventor: Caleb W. Holyoke, Jr., Newark, Del.

[73] Assignee: E. I. Du Pont de Nemours and Company, Wilmington, Del.

[21] Appl. No.: 146,417

[22] Filed: May 5, 1980

[51] Int. Cl.³ ............................................. C07F 7/22
[52] U.S. Cl. .................................. 260/429.7; 71/97; 424/288
[58] Field of Search ...................................... 260/429.7

[56] References Cited

U.S. PATENT DOCUMENTS 3,794,670  2/1974  Peterson ........................... 260/429.7
4,128,429  12/1978  Wyant et al. ................ 260/429.7 X
4,221,811  9/1980  Bueten ........................ 260/429.7 X

FOREIGN PATENT DOCUMENTS 1026405  4/1966  United Kingdom .

OTHER PUBLICATIONS

Chemical Abstracts 56 14324b, (1962).

*Primary Examiner*—Helen M. S. Sneed

[57] ABSTRACT

N,N-diaryl stannanamines such as 1,1,1-tributyl-N-[2-chloro-5-(trifluoromethyl)phenyl]-N-[2,4-dinitro-6-(trifluoromethyl)phenyl] stannanamine are useful as miticides, insecticides, fungicides, ovicides and herbicides.

15 Claims, No Drawings

AGRICULTURAL STANNANAMINES

BACKGROUND OF THE INVENTION

This invention relates to miticidal, insecticidal, fungicidal, ovicidal and herbicidal diarylstannanamines.

Belgian Pat. No. 826,376 discloses pesticidal diphenylamine derivatives of the formula

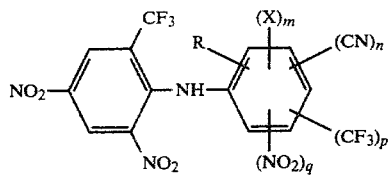

where X and R represent various substituent definitions.

British Pat. No. 1,455,207 discloses a pesticidal diphenylamine of the formula

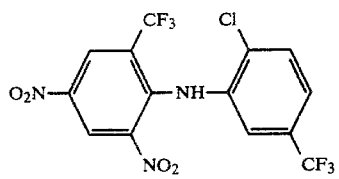

Belgian Pat. No. 846,205 discloses compounds with utility as rodenticides of the formula

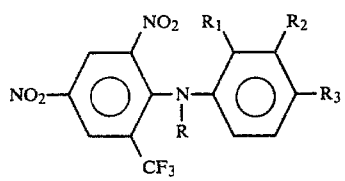

where R, $R_1$, $R_2$ and $R_3$ represent various defined substituents.

Belgian Pat. No. 846,,419 discloses compounds with utility as delayed-action rodenticides.

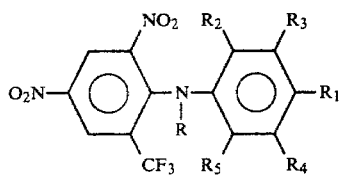

where R, $R_1$, $R_2$, $R_3$, $R_4$ and $R_5$ represent various defined substituents.

European Pat. No. 156 discloses benzotrifluoride derivatives with insecticidal, acaricidal, nematicidal, insect growth retardant, fungicidal and bactericidal activity. These compounds have the formula

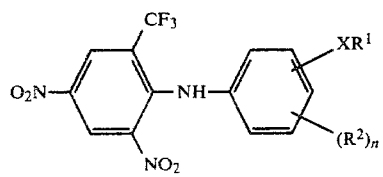

where $R^1$ and $R^2$ represent various defined substituents.

European Pat. No. 4642 discloses compounds useful as insecticides, acaricides, nematocides, fungicides and herbicides of the formula

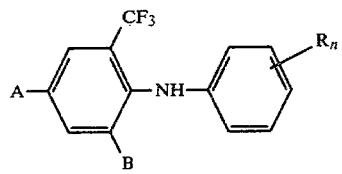

where A, B and R represent various defined substituents.

SUMMARY OF THE INVENTION

This invention relates to novel stannanamines of formula (I), to methods for preparing them, and to compositions and methods for using them to control mites, mite eggs, fungus disease of plants, insects, insect eggs, and/or undesirable vegetation.

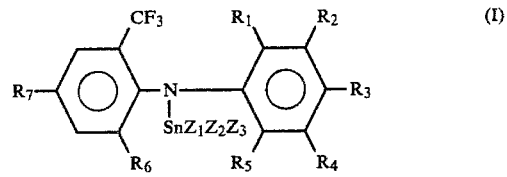

wherein $Z_1$, $Z_2$ and $Z_3$ are independently $C_1$–$C_8$ alkyl, $C_5$–$C_6$ cycloalkyl or phenyl;

$R_1$, $R_3$ and $R_4$ are independently H, F, Cl, Br, $NO_2$, $CF_3$, $OCF_2H$, $OCF_3$, $OCF_2CF_2H$ or $S(O)_kR_9$; and $R_3$ and $R_4$ can be taken together to form —$OCF_2O$— or —$OCF_2OCF_2$—;

$R_2$ is H, F, Cl, Br, $NO_2$, $CF_3$ or $S(O)_kR_9$;

$R_5$ is H, Cl, F, Br or $NO_2$;

$R_6$ is H, $NO_2$ or $CF_3$;

$R_7$ is $NO_2$ or $CF_3$;

$k$ is 0, 1 or 2;

$R_9$ is $C_1$–$C_2$ alkyl optionally substituted with 2–4 atoms of Cl or F.

provided that (1) at least two of $R_1$, $R_2$, $R_3$, $R_4$ and $R_5$ are hydrogen;

(2) no more than two of the substituents $R_1$, $R_2$, $R_3$ and $R_4$ are simultaneously $NO_2$ or $CF_3$;

(3) when two $NO_2$ or two $S(O)_kR_9$ groups are present they are not *ortho* to one another, and further provided that when $R_6$ is $NO_2$, then (a) $R_1$ is H, F or Cl when $R_3$ is other than H, F, or Cl;

(b) when $R_1=R_3=R_5$, then $R_1$, $R_3$ and $R_5$ are either H or F; and (c) $R_5$ is either H or F.

PREFERRED COMPOUNDS

Preferred for reasons of lower cost, and/or greater miticidal, insecticidal, ovicidal, fungicidal and/or herbicidal activity are those compounds of Formula I where independently:

$R_1$ is F, Cl, Br, $CF_3$, $OCF_3$, $OCF_2CF_2H$ or $S(O)_kCF_3$;

$R_2$ is H, F, Cl or Br;

$R_3$ is H, F, Cl, Br or $S(O)_kCF_3$;

$R_4$ is F, Cl, Br, $CF_3$, $OCF_2H$, $OCF_3$, $OCF_2CF_2H$ or $S(O)_kCF_3$;

$R_6$ and $R_7$ are $NO_2$.

More preferred for the same reasons are compounds of Formula I where independently:

$R_1$ and $R_4$ are independently Cl, $CF_3$, $OCF_2H$, $OCF_3$, $OCF_2CF_2H$ or $S(O)_kCF_3$;
$R_3$ is H or $S(O)_kCF_3$;
$R_2$ and $R_5$ are H.

Even more preferred for reasons of even lower cost and/or greater ease of synthesis and/or even higher miticidal, insecticidal, ovicidal, fungicidal and/or herbicidal activity are those compounds of the more preferred group in which $Z_1 = Z_2 = Z_3$.

Specifically preferred for excellent insecticidal, miticidal, ovicidal, fungicidal and/or herbicidal activity are:

1,1,1-tributyl-N-[2-chloro-5-(trifluoromethyl)-phenyl]-N-[2,4-dinitro-6-(trifluoromethyl)phenyl]stannanamine;

1,1,1-tricyclohexyl-N-[2-chloro-5-(trifluoromethyl)-phenyl]-N-[2,4-dinitro-6-(trifluoromethyl)phenyl]stannanamine;

1,1,1-triphenyl-N-[2-chloro-5-(trifluoromethyl)-phenyl]-N-[2,4-dinitro-6-(trifluoromethyl)phenyl]stannanamine.

SYNTHESIS

The compounds of this invention can be prepared by reacting a diphenylamine of Formula II with trisubstituted tin chlorides, $ClSnZ_1Z_2Z_3$, in the presence of an acid acceptor and an inert solvent as outlined in the following equation:

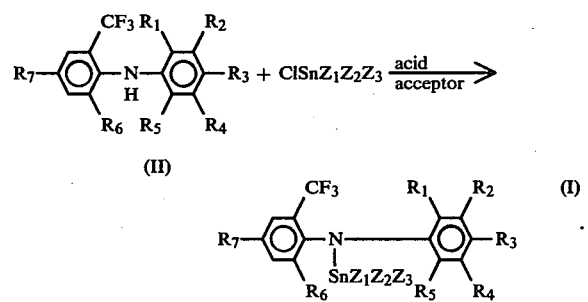

in which $R_1$, $R_2$, $R_3$, $R_4$, $R_5$, $R_6$, $R_7$, $Z_1$, $Z_2$ and $Z_3$ are as previously defined. Organic bases such as N,N-dimethylaniline, triethylamine, trimethylamine, or pyridine or inorganic bases such as sodium or potassium hydroxide sodium or potassium carbonate, or sodium hydride may be used as the acid acceptor. Aprotic solvents such as diethyl ether, tetrahydrofuran (THF), dioxane, methylene chloride, chloroform, or toluene are exemplary of suitable solvents for the reaction. The reaction temperature can be within the range of approximately $-40°$ C. to $80°$ C., preferably approximately $-20°$ C. to $30°$ C. Pressure is not critical; for convenience, ambient pressure is preferred.

The diphenylamines of Formula II used in the reactions described above can be prepared using procedures taught in Belgian Pat. No. 826,376, European Patent Application No. 156, European Patent Application No. 4,642, and West German Offenglegungsschrift No. 2,823,168, the disclosures of which are herein incorporated by reference.

The organotin halides used in preparation of the compounds of Formula I may be prepared by any of several methods well known in the art; such methods have been reviewed in W. P. Newmann, "The Organic Chemistry of Tin", Wiley, London (1970) and references therein.

In the following examples, all parts are by weight and degrees are in centigrade, unless otherwise specified.

EXAMPLE 1

Sodium hydride (0.58 g of a 50% dispersion in mineral oil), washed free of mineral oil (with hexane) under a nitrogen atmosphere was stirred in 25 ml anhydrous tetrahydrofuran (THF). To this cooled slurry was added 4.3 g of N-[2-chloro-5-(trifluoromethyl)phenyl]-2,4-dinitro-6-(trifluoromethyl)benzeneamine in portions. The resulting deep-red solution was cooled to $-10°$ C. and a solution of 3.25 g of tri-n-butyl tin chloride in 25 ml THF was added. The solution was stirred cold for 1 hour; the cooling bath was removed and the reaction was stirred for 1 additional hour.

Fifty ml of hexane was added and the solution was filtered through celite. Then the solvent was removed in vacuum, leaving a red oil which partially solidified on standing. IR major absorbtions at 2900–2800, $cm^{-1}$, 1600 $cm^{-1}$, 1540–1500 $cm^{-1}$, 1340–1300 $cm^{-1}$, 1260–1240 $cm^{-1}$, 1120 $cm^{-1}$, NMR ($CDCl_3$, $\delta$) 8.8–8.4 (doublet of doublets, 2H), 6.9–8.0 (multiplet, 3H), 0.8–1.7 (multiplet, 27H).

TABLE 1

| $R_1$ | $R_2$ | $R_3$ | $R_4$ | $R_5$ | $R_6$ | $R_7$ | $Z_1$ | $Z_2$ | $Z_3$ | m.p.°C. |
|---|---|---|---|---|---|---|---|---|---|---|
| Cl | H | H | $CF_3$ | H | H | $NO_2$ | $-(CH_2)_3CH_3$ | $-(CH_2)_3CH_3$ | $-(CH_2)_3CH_3$ | |
| Cl | H | H | $CF_3$ | H | $NO_2$ | $CF_3$ | $-(CH_2)_3CH_3$ | $-(CH_2)_3CH_3$ | $-(CH_2)_3CH_3$ | |
| Cl | H | H | $CF_3$ | H | $NO_2$ | $CF_3$ | $-(CH_2)_3CH_3$ | $-(CH_2)_3CH_3$ | $-(CH_2)_3CH_3$ | |
| Cl | H | H | $CF_3$ | H | $CF_3$ | $NO_2$ | $-(CH_2)_3CH_3$ | $-(CH_2)_3CH_3$ | $-(CH_2)_3CH_3$ | |
| Cl | H | H | $CF_3$ | H | $CF_3$ | $NO_2$ | $-(CH_2)_3CH_3$ | $-(CH_2)_3CH_3$ | $-(CH_2)_3CH_3$ | |
| Cl | H | H | $CF_3$ | H | $NO_2$ | $NO_2$ | $-(CH_2)_3CH_3$ | $-(CH_2)_3CH_3$ | $-(CH_2)_3CH_3$ | |
| Cl | H | H | $HCF_2O$ | H | $NO_2$ | $NO_2$ | $-(CH_2)_3CH_3$ | $-(CH_2)_3CH_3$ | $-(CH_2)_3CH_3$ | |
| Cl | H | H | $HCF_2CF_2O$ | H | $NO_2$ | $NO_2$ | $-(CH_2)_3CH_3$ | $-(CH_2)_3CH_3$ | $-(CH_2)_3CH_3$ | |
| Cl | H | H | $CH_3S$ | H | $NO_2$ | $NO_2$ | $-(CH_2)_3CH_3$ | $-(CH_2)_3CH_3$ | $-(CH_2)_3CH_3$ | |
| Cl | H | H | $CHCl_2CCl_2S$ | H | $NO_2$ | $NO_2$ | $-(CH_2)_3CH_3$ | $-(CH_2)_3CH_3$ | $-(CH_2)_3CH_3$ | |
| Cl | H | H | $CF_3SO_2$ | H | $NO_2$ | $NO_2$ | $-(CH_2)_3CH_3$ | $-(CH_2)_3CH_3$ | $-(CH_2)_3CH_3$ | |
| Cl | H | H | $C_2H_5S$ | H | $NO_2$ | $NO_2$ | $-(CH_2)_3CH_3$ | $-(CH_2)_3CH_3$ | $-(CH_2)_3CH_3$ | |
| $CF_3O$ | H | H | Cl | H | $NO_2$ | $NO_2$ | $-(CH_2)_3CH_3$ | $-(CH_2)_3CH_3$ | $-(CH_2)_3CH_3$ | |
| $HCF_2CF_2O$ | H | H | Cl | H | $NO_2$ | $NO_2$ | $-(CH_2)_3CH_3$ | $-(CH_2)_3CH_3$ | $-(CH_2)_3CH_3$ | |
| $CHCl_2CCl_2S$ | H | H | Cl | H | $NO_2$ | $NO_2$ | $-(CH_2)_3CH_3$ | $-(CH_2)_3CH_3$ | $-(CH_2)_3CH_3$ | |
| $CF_3S$ | H | H | H | H | $NO_2$ | $NO_2$ | $-(CH_2)_3CH_3$ | $-(CH_2)_3CH_3$ | $-(CH_2)_3CH_3$ | |

TABLE 1-continued $$\underset{R_6}{\underset{|}{R_7}} \overset{CF_3}{\bigcirc} - \underset{\underset{SnZ_1Z_2Z_3}{|}}{N} - \underset{R_5}{\overset{R_1}{\bigcirc}} \overset{R_2}{\underset{R_4}{\bigcirc}} R_3$$

| $R_1$ | $R_2$ | $R_3$ | $R_4$ | $R_5$ | $R_6$ | $R_7$ | $Z_1$ | $Z_2$ | $Z_3$ | m.p.°C. |
|---|---|---|---|---|---|---|---|---|---|---|
| $CH_3SO_2$ | H | H | H | H | $NO_2$ | $NO_2$ | $-(CH_2)_3CH_3$ | $-(CH_2)_3CH_3$ | $-(CH_2)_3CH_3$ | |
| $CF_3$ | H | H | H | H | $NO_2$ | $NO_2$ | $-(CH_2)_3CH_3$ | $-(CH_2)_3CH_3$ | $-(CH_2)_3CH_3$ | |
| H | H | $CF_3S$ | H | H | $NO_2$ | $NO_2$ | $-(CH_2)_3CH_3$ | $-(CH_2)_3CH_3$ | $-(CH_2)_3CH_3$ | |
| Cl | H | $-OCF_2O-$ | | H | $NO_2$ | $NO_2$ | $-(CH_2)_3CH_3$ | $-(CH_2)_3CH_3$ | $-(CH_2)_3CH_3$ | |
| Cl | H | $-OCF_2OCF_2-$ | | H | $NO_2$ | $NO_2$ | $-(CH_2)_3CH_3$ | $-(CH_2)_3CH_3$ | $-(CH_2)_3CH_3$ | |
| H | H | $HCF_2CF_2O$ | H | H | $NO_2$ | $NO_2$ | $-(CH_2)_3CH_3$ | $-(CH_2)_3CH_3$ | $-(CH_2)_3CH_3$ | |
| H | H | $CH_3S$ | H | H | $NO_2$ | $NO_2$ | $-(CH_2)_3CH_3$ | $-(CH_2)_3CH_3$ | $-(CH_2)_3CH_3$ | |
| H | H | $C_2H_5SO_2$ | H | H | $NO_2$ | $NO_2$ | $-(CH_2)_3CH_3$ | $-(CH_2)_3CH_3$ | $-(CH_2)_3CH_3$ | |
| H | $CF_3$ | Cl | H | H | $NO_2$ | $NO_2$ | $-(CH_2)_3CH_3$ | $-(CH_2)_3CH_3$ | $-(CH_2)_3CH_3$ | |
| Cl | H | Cl | H | H | $NO_2$ | $NO_2$ | $-(CH_2)_3CH_3$ | $-(CH_2)_3CH_3$ | $-(CH_2)_3CH_3$ | |
| F | H | F | H | F | $NO_2$ | $NO_2$ | $-(CH_2)_3CH_3$ | $-(CH_2)_3CH_3$ | $-(CH_2)_3CH_3$ | |
| Cl | H | H | $NO_2$ | H | $NO_2$ | $NO_2$ | $-(CH_2)_3CH_3$ | $-(CH_2)_3CH_3$ | $-(CH_2)_3CH_3$ | |
| H | Cl | Cl | H | H | $NO_2$ | $NO_2$ | $-(CH_2)_3CH_3$ | $-(CH_2)_3CH_3$ | $-(CH_2)_3CH_3$ | |
| H | F | H | H | F | $NO_2$ | $NO_2$ | $-(CH_2)_3CH_3$ | $-(CH_2)_3CH_3$ | $-(CH_2)_3CH_3$ | |
| H | $CHF_2CF_2S$ | H | H | H | $NO_2$ | $NO_2$ | $-(CH_2)_3CH_3$ | $-(CH_2)_3CH_3$ | $-(CH_2)_3CH_3$ | |
| H | $CHF_2CF_2SO_2$ | H | H | H | $NO_2$ | $NO_2$ | $-(CH_2)_3CH_3$ | $-(CH_2)_3CH_3$ | $-(CH_2)_3CH_3$ | |
| H | $CH_3S$ | H | H | H | $NO_2$ | $NO_2$ | $-(CH_2)_3CH_3$ | $-(CH_2)_3CH_3$ | $-(CH_2)_3CH_3$ | |
| Cl | H | $CF_3O$ | H | H | $NO_2$ | $NO_2$ | $-(CH_2)_3CH_3$ | $-(CH_2)_3CH_3$ | $-(CH_2)_3CH_3$ | |
| Br | H | Br | H | H | $NO_2$ | $NO_2$ | $-(CH_2)_3CH_3$ | $-(CH_2)_3CH_3$ | $-(CH_2)_3CH_3$ | |
| Cl | H | $NO_2$ | H | H | $NO_2$ | $NO_2$ | $-(CH_2)_3CH_3$ | $-(CH_2)_3CH_3$ | $-(CH_2)_3CH_3$ | |
| $NO_2$ | H | Cl | H | H | $NO_2$ | $NO_2$ | $-(CH_2)_3CH_3$ | $-(CH_2)_3CH_3$ | $-(CH_2)_3CH_3$ | |
| H | H | H | F | H | $NO_2$ | $NO_2$ | $-(CH_2)_3CH_3$ | $-(CH_2)_3CH_3$ | $-(CH_2)_3CH_3$ | |
| H | H | H | Br | H | $NO_2$ | $NO_2$ | $-(CH_2)_3CH_3$ | $-(CH_2)_3CH_3$ | $-(CH_2)_3CH_3$ | |
| Cl | H | H | Cl | H | $NO_2$ | $NO_2$ | $-(CH_2)_3CH_3$ | $-(CH_2)_3CH_3$ | $-(CH_2)_3CH_3$ | |
| Cl | H | H | $CF_3$ | H | $NO_2$ | $NO_2$ | $-(CH_2)_3CH_3$ | $-(CH_2)_3CH_3$ | $-(CH_2)_3CH_3$ | red oil/solid |
| Cl | H | H | $CF_3$ | H | $NO_2$ | $NO_2$ | $-CH_3$ | $-CH_3$ | $-CH_3$ | |
| Cl | H | H | $CF_3$ | H | $NO_2$ | $NO_2$ | $-(CH_2)_7CH_3$ | $-(CH_2)_7CH_3$ | $-(CH_2)_7CH_3$ | |
| Cl | H | H | $CF_3$ | H | $NO_2$ | $NO_2$ | $-(CH_2)_3CH_3$ | $-(CH_2)_3CH_3$ | $-(CH_2)_7CH_3$ | |
| Cl | H | H | $CF_3$ | H | $NO_2$ | $NO_2$ | $-(CH_2)_3CH_3$ | -cyclohexyl | -cyclohexyl | |
| Cl | H | H | $CF_3$ | H | $NO_2$ | $NO_2$ | -cyclohexyl | -cyclohexyl | -cyclohexyl | |
| Cl | H | H | $CF_3$ | H | $NO_2$ | $NO_2$ | -cyclopentyl | -cyclopentyl | -cyclopentyl | |
| Cl | H | H | $CF_3$ | H | $NO_2$ | $NO_2$ | -phenyl | -phenyl | -phenyl | |

FORMULATION

Useful formulations of the compounds of Formula (I) can be prepared in conventional ways. They include dusts, solutions, suspensions, emulsions, wettable powders, emulsifiable concentrates and the like. Many of these may be applied directly to the plant. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J.. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, promote sticking, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, Apr. 27, 1971, Col, 5, Line 36 through Col. 7, Line 70 and Ex. 1-4, 17, 106, 123-140;

R. R. Shaffer, U.S. Pat. No. 3,560,616 Feb. 2, 1971, Col. 3, Line 48 through Col. 7, Line 26 and Examples 3-9, 11-18;

E. Somers, "Formulation", Chapter 6 in Torgeson, "Fungicides", Vol, I, Academic Press, New York, 1967.

EXAMPLE A

| Wettable Powder | |
|---|---|
| 1,1,1-tributyl-N-[2-chloro-5-(trifluoromethyl)phenyl]-N-[2,4-dinitro-6-(trifluoromethyl)phenyl]stannanamine | 30% |
| Sodium alkylnaphthalene sulfonate | 2% |
| Low viscosity methyl cellulose | 2% |
| Diatomaceous earth | 66% |

The active ingredient is dissolved in methylene chloride and sufficient methylene chloride is added to make a sprayable solution. The solution is sprayed onto the diluent with agitation in a double-cone blender. The solvent is removed by heating. After addition of the wetting agent and the dispersant, the mixture is blended and hammer-milled, then reblended and sifted through a U.S.S. No. 50 sieve (0.3 mm opening) before packaging.

All compounds of the invention may be formulated in the same manner, and dispersed in water for application.

EXAMPLE B

| Dust | |
|---|---|
| Wettable powder of Example A | 10% |
| Pyrophyllite (powder) | 90% |

The wettable powder and the pyrophyllite diluent are thoroughly blended and then packaged. The product is suitable for use as a dust.

EXAMPLE C

| Solution | |
|---|---|
| 1,1,1-Tributyl-N-[2-chloro-5-(trifluoromethyl)phenyl]-N-[2,4-dinitro-6-(trifluoromethyl)phenyl]stannanamine | 30% |
| Dimethylformamide | 70% |

The ingredients are combined and stirred to produce a solution, which can be used for low volume applications.

EXAMPLE D

| Emulsifiable Concentrate | |
|---|---|
| 1,1,1-Tributyl-N-[2-chloro-5-(trifluoromethyl)phenyl]-N-[2,4-dinitro-6-(trifluoromethyl)phenyl]stannanamine | 20% |
| Blend of oil soluble sulfonates and polyoxyethylene esters | 4% |
| Xylene | 76% |

The ingredients are combined and stirred with gentle warming to speed solution. A fine screen filter is included in the packaging operation to insure the absence of any extraneous undissolved material in the product.

EXAMPLE E

| Granule | |
|---|---|
| Wettable powder of Example A | 15% |
| Gypsum | 69% |
| Potassium sulfate | 16% |

The ingredients are blended in a rotating mixer and water sprayed on to accomplish granulation. When most of the material has reached the desired range of 1.0 to 0.42 mm (U.S.S. No. 18 to 40 sieves), the granules are removed, dried and screened. Oversize material is crushed to produce additional material in the desired range. These granules contain 4.5% active ingredient.

EXAMPLE F

| Aqueous Suspension | |
|---|---|
| 1,1,1-Tributyl-N-[2-chloro-5-(trifluoromethyl)phenyl]-N-[2,4-dinitro-6-(trifluoromethyl)phenyl]stannanamine | 25% |
| Hydrated attapulgite | 3% |
| Crude calcium ligninsulfonate | 10% |
| Sodium dihydrogen phosphate | 0.5% |
| Water | 61.5% |

The ingredients are ground together in a ball or roller mill until the solid particles have been reduced to diameters under 10 microns.

UTILITY

The compounds of this invention may be used in several ways. First, they are active as miticides and mite ovicides and may be used to protect plants from damage caused by these pests. More specifically, fruits, field crops, vegetables and ornamentals can be protected.

When mite eggs or mites come into contact with the compounds of this invention, either in the form of direct spray or in the case of motile forms by walking over treated surfaces, they are killed if they have been exposed to a sufficiently high dosage. While most plants are able to tolerate the presence of very small numbers of mites without adverse effect, the reproductive capacity of these pests is enormous. Generally, mite populations rapidly build up, easily out-stripping parasite and predator capabilities for control. Growers noting rapid mite build-up must take immediate action to prevent damage to economically important crops.

The method of this invention, namely, contacting mites or mite eggs with an effective concentration, is a most desirable method for control of these pests. This may be accomplished by applying an effective amount of a compound of this invention to the locus of infestation, to the area to be protected or to the pests themselves.

The quantity of compound needed for miticidal activity will vary depending on the specific situation; generally, a very small quantity is required. Among the variables that must be considered in deciding on the quantity of chemical to be used are the specific compound itself, the specific mite to be controlled, weather conditions, the type of crop, the stage of development of the crop, the volume of spray applied, population pressure, and the interval between applications. For plant protection, solutions or suspensions contain as little as 2.5 ppm of active ingredient in a spray solution may prove effective in a given set of circumstances. For field usage, however, in high-volume applications, aqueous spray preparations containing 5–2500 ppm of active ingredient are generally useful. Preferred are suspensions containing 20–500 ppm, and most preferred are those containing 80–320 ppm. On an area basis, in general, 0.03 to 5.5 kilograms of active ingredient per hectare are acceptable, preferably 0.03 to 3 kilograms, and most preferably, 0.06 to 2 kg. When applied in an orchard, spraying is continued until run-off is observed.

The compounds are especially suited for the protection of living plants such as fruit-bearing trees, nut-bearing trees, ornamental trees, forest trees, vegetable crops, horticultural crops (including ornamentals, small fruits and berries) and grain and seed crops. Apple trees, peach trees, cotton, citrus trees, bean and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites", and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Byrobia praetiosa* (clover mite) which attacks clover, alfalfa and other crops; and *Aceria Neocynodomis* which attacks grasses and other plants.

The compounds of this invention are useful for the control of insects throughout their various developmental stages. The insects or insect eggs are controlled by applying the material in a convenient formulation to the locus of infestation, to the area to be protected, or to the pests themselves. For the control of insects in agricultural crops, the compound is generally applied to the foliage or other plant parts which are to be protected. Effective amounts to be applied depend on the species to be controlled, its life stage, its size and location and other variables. In general, 0.1 to 10 kg/ha may be required for insect control in agriculture with rates of 0.25 to 4 kg/ha usually being sufficient. Preferable rates in large scale operations are in the range of 0.3 to 2 kg/ha.

The insect species that may be controlled during their various developmental stages by the insecticidal action of the compounds of this invention include, but are not limited to, *Spodoptera exigua* (beetarmyworm), *Spodoptera eridania* (southern armyworm), *Spodoptera frugiperda* (fall armyworm), *Heliothis zea* (bollworm), *Heliothis virescens* (tobacco budworm), and *Trichoplusia ni* (cabbage looper).

These compounds are especially useful for controlling adult mosquitos, mosquito larvae, and ticks including, but not limited to, *Rhipicephalus sanguineus* (brown dog tick) and *Dermacentor variabiles* (American dog tick).

Motile stages of insects that may be controlled include, but are not limited to, *Aphis fabae* (bean aphid), *Myzus persicae* (green peach aphid), *Melanopus fermurrubrum* (redlegged grasshopper), and *Musca domestica* (house fly).

EXAMPLE 2

Test units consisted of plant pots containing two red kidney bean plants in the two-leaf stage per pot. The plants were infested with two spotted mites and sprayed to run-off with dispersions of 1,1,1-tributyl-N-[2-chloro-5-trifluoromethyl)phenyl]-N-[2,4-dinitro-6-(trifluoromethyl)phenyl]stannanamine at the indicated concentrations. Dispersions were made by dissolving weighed quantities of the active ingredients in 10 ml of acetone and then diluting to volume with water containing 1:3000 of a surfactant, DuPonol ® (a tradename of E. I. du Pont de Nemours and Co. for sodium alcohol sulfonate). Mortality was evaluated two days after spraying.

TABLE 2

| Compound | % Spray Concentration | % Mortality (2 days) |
| --- | --- | --- |
| 1,1,1-tributyl-N-[2-chloro-5-(trifluoromethyl)phenyl]-N-[2,4-dinotro-6-(trifluoromethyl)phenyl]stannanamine | .00050 | 99 |

EXAMPLE 3

Egg masses of the beet armyworm (*Spodoptera exigua*), laid on cellophane, each containing 50–75 eggs, were placed in petri dishes and sprayed with solutions of 1,1,1-tributyl-N-[2-chloro-5-(trifluoromethyl)phenyl]-N-[2,4-dinitro-6-(trifluoromethyl)phenyl]stannanamine. Dispersions were made by dissolving weighed quantities of the active ingredient in acetone. Three days later, percent control (% eggs failing to hatch) was determined.

TABLE 3

| Compound | % Spray Concentration | Control (3 days) |
| --- | --- | --- |
| 1,1,1-tributyl-N-[2-chloro-5-(trifluoromethyl)phenyl]-N-[2,4-dinitro-6-(trifluoromethyl)phenyl]stannanamine | .00250 | 100 |

EXAMPLE 4

Tobacco budworm (*Helrothis virescens*) larvae were treated topically with 1,1,1-tributyl-N-[2-chloro-5-(trifluoromethyl)phenyl]-N-[2,4-dinitro-6-(trifluoromethyl)phenyl]stannanamine. One microliter of the indicated concentration was applied to the dorsoprothoracic area of each larva tested. Stock solutions were prepared by dissolving appropriately weighed quantities of active ingredient in predetermined quantities of acetone. Further diluting with acetone yielded the desired concentrations. After treatment, the larvae were returned to cups containing artificial diet (rearing substrate) and kept in a growth room at 26°±0.5° C. and 50–60% RH. Mortality readings were taken at 48 hours.

TABLE 4

| Compound | μg/larva | % Mortality |
| --- | --- | --- |
| 1,1,1-tributyl-N-[2-chloro-5-(trifluoromethyl)phenyl]-N-[2,4-dinitro-6-(trifluoromethyl)phenyl]stannanamine | 1 | 93 |

EXAMPLE 5

Beet armyworm (*Spodoptera exigua*) larvae were treated topically with 1,1,1-tributyl-N-[2-chloro-5-(trifluoromethyl)phenyl]-N-[2,4-dinitro-6-(trifluoromethyl)phenyl]stannanamine. One microliter of the indicated concentration was applied to the dorsoprothoracic area of each larva tested. Stock solutions were prepared by dissolving appropriately weighed quantities of active ingredient in predetermined quantities of acetone. Further diluting with acetone yielded the desired concentrations. After treatment, the larvae were returned to cups containing artificial diet (rearing substrate) and kept in a growth room at 26°±0.5° C. and 50–60% RH. Mortality readings were taken at 48 hours.

TABLE 5

| Compound | μg/larvae | % Mortality |
| --- | --- | --- |
| 1,1,1-tributyl-N-[2-chloro-5-(trifluoromethyl)phenyl]-N-[2,4-dinitro-6-(trifluoromethyl)phenyl]stannanamine | 5.0 | 100 |

EXAMPLE 6

Twenty-five house fly adults are secured in screened stainless steel ring cages and treated with acetone dispersions of 1,1,1-tributyl-N-[2-chloro-5-(trifluoromethyl)phenyl]-N-[2,4-dinitro-6-(trifluoromethyl)phenyl]-stannanamine at the indicated concentrations. The stock dispersion is prepared by dissolving appropriately weighted quantities of acetone. Further diluting with acetone yields the desired concentration. After treating, the units are kept in a room maintained at 25°±2° C., 50% RH. Results are recorded at the end of 1 day.

TABLE 6

| Compound | Concentration % | % Mortality |
| --- | --- | --- |
| 1,1,1-tributyl-N-[2-chloro-5-(trifluoromethyl)phenyl]-N-[2,4-dinitro-6-(trifluoromethyl)phenyl]stannanamine | .01 | 100 |

The compounds of this invention are also useful as plant disease control agents. They are effective for the control of a broad spectrum of plant diseases as represented by, but not limited to, soil-borne fungal pathogen *Rhizoctonia solani*, foliar pathogens, *Puccinia graminis*, *Erisyphe cichoracearum*, *Venturia inaequalis* and *Phytophthora infestans*, and the seed-borne fungus *Helminthosporium oryzae*. Diseases of a wide variety of ornamental, vegetable, cereal and fruit crops are controlled by the compound of this invention.

Disease control is accomplished by applying the compound to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for this compound will be influenced by many factors of the environment and must be determined under use conditions. Foliage can normally be protected when treated at a rate of from 1 to 500 ppm of active ingredient. Plants growing in soil treated at a concentration of from 0.1 to about 20 kg/ha can be protected from disease. Seed and seedlings can normally be protected when seed is treated at a rate of from 0.06 to about 3 grams per kilogram of seed.

EXAMPLE 7

Rice seed infected with *Helminthosporium oryzae* are treated with the compound of this invention at a rate of 1.3 g per kilogram of seed. This is accomplished by soaking infected seed for 1 minute in a suspension of the indicated compound dissolved in a solution containing 4% glycerine, 4% water, 0.02% Tween ®20*, and 92% acetone. Treated seed are placed on moist blotters and enclosed in plastic bags for 18 days at which time disease ratings are made based on percent germination. As shown in the following table, the compound of this invention provided excellent disease control, as treated seed had a high percentage germination in contrast to untreated seed which did not germinate. Phytotoxicity in the form of growth reduction was observed on germinated seedlings in association with disease control.

*Tween ®20 is a trademark of ICI Americas, Inc. and consists of polyoxyethylene (20) sorbitan monolaurate.

TABLE 7

| Compound | % Control of rice Hellminthosporium in a seed treatment test |
| --- | --- |
| 1,1,1-tributyl-N-[2-chloro-5-(trifluoromethyl)phenyl]-N-[2,4-dinitro-6-(trifluoromethyl)phenyl]stannanamine | 100 (G)** |

**G = growth reduction

EXAMPLE 8

*Rhizoctonia solani*-infested soil was placed in a 900 cc cup. The compound of this invention was mixed at a rate of 15 kg/ha in a section 2" wide×2"deep×4" long to simulate an in-the-row application. Five cotton seeds were planted in the treated soil. After 8 days, the cotton plants were removed and rated for disease control. Phytotoxicity in the form of growth reduction was observed on the plants in association with disease control.

TABLE 8

| Compound | % *Rhizoctonia solani* control |
| --- | --- |
| 1,1,1-tributyl-N-[2-chloro-5-(trifluoromethyl)phenyl]-N-[2,4-dinitro-6-(trifluoro- | 100 (G)* |

TABLE 8-continued

| Compound | % Rhizoctonia solani control |
|---|---|
| methyl)phenyl]stannanamine | 5 |

*G = growth reduction

EXAMPLE 9

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on apple seedlings. The following day, the plants are inoculated with a spore suspension of the fungus *Venturia inaequalis* and incubated in a growth room for 10–12 days. Disease ratings are then made. As shown in the following table, the compound of this invention provided excellent disease control, as treated plants had no apple scab lesions in contrast to untreated plants which were covered with scab lesions. Phytotoxicity in the form of foliar burn was observed on the plants in association with disease control.

TABLE 9

| Compound | % Control apple scab in a preventive test |
|---|---|
| 1,1,1-tributyl-N-[2-chloro-5-(trifluoromethyl)phenyl]-N-[2,4-dinitro-6-(trifluoromethyl)phenyl]stannanamine | 100 (B)* |

*B = burn

EXAMPLE 10

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on apple seedlings. The following day, ½ inch of simulated rainfall is applied to the foliage of the plants. When the foliage is dry, the plants are inoculated with a spore suspension of the fungus *Venturia inaequalis* and incubated in a growth room for 10–12 days. Disease ratings are then made. As shown in the following table, the compound of this invention provided excellent disease control, as treated plants had no apple scab lesions in contrast to untreated plants which were covered with scab lesions. Phytotoxicity in the form of foliar burn was observed on the plants in association with disease control.

TABLE 10

| Compound | % Control of apple scab in a residual wash-off test |
|---|---|
| 1,1,1-tributyl-N-[2-chloro-5-(trifluoromethyl)phenyl]-N-[2,4-dinitro-6-(trifluoromethyl)phenyl]stannanamine | 100 (B)* |

*B = burn

EXAMPLE 11

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on apple seedlings. When the foliage is dry, the plants are exposed to 3500 foot candles of light from a xenon arc source for a period of 16 hours. This light source approximates the spectrum of natural sunlight, and is used to assess photostability of the compounds of this invention on plant foliage. The following day, the plants are inoculated with a spore suspension of the fungus *Venturia inaequalis* and incubated in a growth room for 10–12 days. Disease ratings are then made. As shown in the following table, the compound of this invention provided excellent disease control, as the treated plants had no apple scab lesions in contrast to untreated plants which were covered with scab lesions. Phytotoxicity in the form of foliar burn was observed on the plants in association with disease control.

TABLE 11

| Compound | % control apple scab in a photostability test |
|---|---|
| 1,1,1-tributyl-N-[2-chloro-5-(trifluoromethyl)phenyl]-N-[2,4-dinitro-6-(trifluoromethyl)phenyl]stannanamine | 100 (B)* |

*B = burn

EXAMPLE 12

A compound of this invention is dissolved in acetone in an amount equal to 6% of the final volume and then suspended at a concentration of 20 ppm in purified water containing 25 ppm of the surfactant Alkanol® XC (sodium alkyl naphthalane sulfonate). This suspension is sprayed to the point of run-off on cucumber seedlings. The following day, the plants are inoculated with a spore suspension of the fungus *Erysiphe cichoracearum* and incubated in a growth room for 7 days. Disease ratings are then made. As shown in the following table, the compound of this invention provided excellent disease control, as treated plants had little powdery mildew in contrast to untreated plants which were covered with powdery mildew. Phytotoxicity in the form of foliar burn was observed on the plants in association with disease control.

TABLE 12

| Compound | % control cucumber powdery mildew in a preventive test |
|---|---|
| 1,1,1-tributyl-N-[2-chloro-5-(trifluoromethyl)phenyl]-N-[2,4-dinitro-6-(trifluoro- | 94 (B)* |

TABLE 12-continued

| Compound | % control cucumber powdery mildew in a preventive test |
|---|---|
| methyl)phenyl]stannanamine | |

*B = burn

EXAMPLE 13

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. The following day, the plants are inoculated with a spore suspension of *Puccinia graminis* var. *tritici* and incubated in a saturated humidity chamber at 20° C. for 24 hours and then in a growth room for an additional 7 days, when disease ratings were made. As shown in the following table, the compound of this invention provided excellent disease control. Treated plants had no rust pustules while the untreated plants had numerous rust pustules on each leaf.

TABLE 13

| Compound | % control wheat rust in a preventive test |
|---|---|
| 1,1,1-tributyl-N-[2-chloro-5-(trifluoromethyl)phenyl]-N-[2,4-dinitro-6-(trifluoromethyl)phenyl]stannanamine | 100 |

EXAMPLE 14

A compound of this invention is dissolved in acetone in an amount equal to 6% of the final volume and then suspended at a concentration of 20 ppm in purified water containing 25 ppm of the surfactant Alkanol ®· XC (sodium alkyl naphthalene sulfonate). This suspension is sprayed to the point of run-off on wheat seedlings. The following day, ½ inch of simulated rainfall is applied to the foliage of the plants. When the foliage is dry, the plants are inoculated with a spore suspension of *Puccinia graminis* var. *tritici* and incubated in a saturated humidity chamber at 20° C. for 24 hours and then in a growth room for an additional 7 days, when disease ratings were made. As shown in the following table, the compound of this invention provided excellent disease control. Treated plants had no rust pustules while the untreated plants had numerous rust pustules on each leaf.

TABLE 14

| Compound | % control wheat rust in a residual wash off test |
|---|---|
| 1,1,1-tributyl-N-[2-chloro-5-(trifluoromethyl)phenyl]-N-[2,4-dinitro-6-(trifluoromethyl)phenyl]stannanamine | 100 |

EXAMPLE 15

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. When the foliage is dry, the plants are exposed to 3500 foot candles of light from a xenon arc source for a period of 16 hours. This light source approximates the spectrum of natural sunlight, and is used to assess photostability of the compound of this invention on plant foliage. The following day, the plants are inoculated with a spore suspension of *Puccinia graminis* var. *tritici* and incubated in a saturated humidity chamber at 20° C. for 24 hours and then in a growth room for an additional 7 days, when disease ratings were made. As shown in the following table, the compound of this invention provided excellent disease control. Treated plants had few rust pustules while the untreated plants had numerous rust pustules on each leaf.

TABLE 15

| Compound | % control wheat rust in a photostability test |
|---|---|
| 1,1,1-tributyl-N-[2-chloro-5-(trifluoromethyl)phenyl]-N-[2,4-dinitro-6-(trifluoromethyl)phenyl]stannanamine | 94 |

EXAMPLE 16

A compound of this invention is dissolved in acetone in an amount equal to 6% of the final volume and then suspended at a concentration of 5 ppm in purified water containing 25 ppm of the surfactant Alkanol ® XC (sodium alkyl naphthalene sulfonate). This suspension is sprayed to the point of run-off on tomato seedlings. The following day, the plants are inoculated with a spore suspension of the fungus *Phytophthora infestans* and incubated in a growth room for 4 days. Disease ratings are then made. As shown in the following table, the compound of this invention provided excellent disease control, as treated plants had few late blight lesions in contrast to untreated plants which were covered with lesions. Phytotoxicity in the form of foliar burn was observed on the plants in association with disease control.

EXAMPLE 16

| Compound | % control tomato late blight in a preventive test |
|---|---|
| 1,1,1-tributyl-N-[2-chloro-5-(trifluoromethyl)phenyl]-N-[2,4-dinitro-6-(trifluoromethyl)phenyl]stannanamine | (B)* |

EXAMPLE 17

A compound of this invention is dissolved in acetone in an amount equal to 6% of the final volume and then suspended at a concentration of 5 ppm in purified water containing 25 ppm of the surfactant Alkanol ® XC (sodium alkyl naphthalene sulfonate). This suspension is sprayed to the point of run-off on tomato seedlings. When the foliage is dry, the plants are exposed to 3500 foot candles of light from a xenon arc source for a period of 16 hours. This light source approximates the spectrum of natural sunlight, and is used to assess photostability of the compound of this invention on plant foliage. The following day, the plants are inoculated with a spore suspension of the fungus *Phytophthora*

*infestans* and incubated in a growth room for 4 days. Disease ratings are then made. As shown in the following table, the compound of this invention provided excellent disease control, as treated plants had few late blight lesions in contrast to untreated plants which were covered with lesions. Phytotoxicity in the form of foliar burn was observed on the plants in association with disease control.

TABLE 17

| Compound | % control tomato late blight in a photo-stability test |
|---|---|
| 1,1,1-tributyl-N-[2-chloro-5-(trifluoromethyl)phenyl]-N-[2,4-dinitro-6-(trifluoromethyl)phenyl]stannanamine | 50 (B)* |

*B = burn

Some of the compounds of this invention are also useful as postemergence herbicides.

The precise amount of the compounds of Formula I to be used in any given situation will vary according to the particular end result desired, the use involved, the crop and weed species, and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.5 to about 20 kilograms per hectare. The lower rates in this range will generally be selected on lighter soils, soils low in organic matter content, for selective weed control in crops, or in situations where maximum persistance is not necessary.

Herbicidal activity of the subject compounds was discovered in a number of greenhouse tests. The test procedure was as follows

TEST PROCEDURE

Seeds of crabgrass (Digitaria spp.), barnyard-grass (*Echinochloa crusgalli*), wild oats (*Avena fatua*), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment. The ratings are based on a numerical scale extending from 0=no injury, to 10=complete kill. The accompanying descriptive symbols have the following meanings; B=burn; G=growth retardation; C=chlorosis/necrosis. The data in Table 18 demonstrate the herbicidal, properties of the compound of this invention.

TABLE 18

| kg/ha | 1,1,1-tributyl-N-[2-chloro-5-(trifluoromethyl)phenyl-N-[2,4-dinitro-6-(trifluoromethyl)-phenyl]stannamine 2 |
|---|---|
| POST-EMERGENCE | |
| BUSHBEAN | 5B |
| COTTON | 9B |
| MORNINGGLORY | 10B |
| COCKLEBUR | 10B |
| CASSIA | 10B |
| NUTSEDGE | 1B |
| CRABGRASS | 3B |
| BARNYARDGRASS | 9B |
| WILD OATS | 5B |
| WHEAT | 5B |
| CORN | 6B |
| SOYBEAN | 2B, 7G |
| RICE | 6B |
| SORGHUM | 5B |
| PRE-EMERGENCE | |
| MORNINGGLORY | 2G |
| COCKLEBUR | — |
| CASSIA | 2C |
| NUTSEDGE | 0 |
| CRABGRASS | 0 |
| BARNYARDGRASS | 2C |
| WILD OATS | 1C |
| WHEAT | 0 |
| CORN | 0 |
| SOYBEAN | 0 |
| RICE | 2C |
| SORGHUM | 2G |

What is claimed is:
1. A compound of the formula

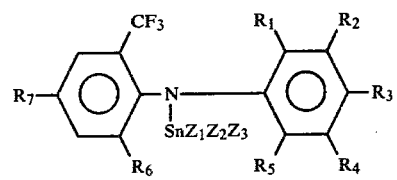

wherein $Z_1$, $Z_2$ and $Z_3$ are independently $C_1$–$C_8$ allyl, $C_5$–$C_6$ cycloalkyl or phenyl;

$R_1$, $R_3$ and $R_4$ are independently H, F, Cl, Br, $NO_2$, $CF_3$, $OCF_2H$, $OCF_3$, $OCF_2CF_2H$ or $S(O)_kR_9$; and $R_3$ and $R_4$ can be taken together to form —$OCF_2O$— or —$OCF_2OCF_2$—;

$R_2$ is H, F, Cl, Br, $NO_2$, $CF_3$ or $S(O)_kR_9$;

$R_5$ is H, Cl, F, Br or $NO_2$;

$R_6$ is H, $NO_2$ or $CF_3$;

$R_7$ is $NO_2$ or $CF_3$;

k is 0, 1 or 2;

$R_9$ is $C_1$–$C_2$ alkyl, optionally substituted with 2–4 Cl or F provided that
(1) at least two of $R_1$, $R_2$, $R_3$, $R_4$ and $R_5$ are hydrogen;
(2) no more than two of the substituents $R_1$, $R_2$, $R_3$ and $R_4$ are simultaneously $NO_2$ or $CF_3$;
(3) when two $NO_2$ or two $S(O)_kR_9$ groups are present they are not ortho to one another, and further provided that when $R_6$ is $NO_2$, then
(a) $R_1$ is H, F or Cl when $R_3$ or other than H, F, or Cl;
(b) when $R_1$=$R_3$=$R_5$, then $R_1$, $R_3$ and $R_5$ are either H or F; and
(c) $R_5$ is either H or F.

2. A compound of claim 1 wherein $R_1$ is F, Cl, Br, $CF_3$, $OCF_2H$, $OCF_3$, $OCF_2CF_2H$ or $S(O)_kCF_3$.

3. A compound of claim 1 wherein $R_2$ is H, F, Cl or Br.

4. A compound of claim 1 wherein $R_3$ is H, F, Cl, Br or $S(O)_kCF_3$.

5. A compound of claim 1 wherein $R_4$ is F, Cl, Br, $CF_3$, $OCF_2H$, $OCF_3$, $OCF_2CF_2H$ or $S(O)_kCF_3$.

6. A compound of claim 1 wherein $R_6$ and $R_7$ are $NO_2$.

7. A compound of claim 1 wherein $R_1$ and $R_4$ are independently Cl, $CF_3$, $OCF_2H$, $OCF_3$, $OCF_2CF_2H$ or $S(O)_kCF_3$.

8. A compound of claim 1 wherein $R_3$ is H or $S(O)_kCF_3$.

9. A compound of claim 1 wherein $R_2$ and $R_5$ are H.

10. A compound of claim 7 where $Z_1$, $Z_2$ and $Z_3$ are identical.

11. A compound of claim 8 where $Z_1$, $Z_2$ and $Z_3$ are identical.

12. A compound of claim 9 where $Z_1$, $Z_2$ and $Z_3$ are identical.

13. The compound of claim 1 which is 1,1,1-tributyl-N-[2-chloro-5-(trifluoromethyl)phenyl]-N-[2,4-dinitro-6-(trifluoromethyl)phenyl]stannanamine.

14. The compound of claim 1 which is 1,1,1-tricyclohexyl-N-[2-chloro-5-(trifluoromethyl)phenyl]-N-[2,4-dinitro-6-(trifluoromethyl)phenyl]stannanamine.

15. The compound of claim 1 which is 1,1,1-triphenyl-N-[2-chloro-5-(trifluoromethyl)phenyl]-N-[2,4-dinitro-6-(trifluoromethyl)phenyl]stannanamine.

* * * * *